United States Patent [19]

Aoyagi

[11] Patent Number: 5,385,143
[45] Date of Patent: Jan. 31, 1995

[54] APPARATUS FOR MEASURING PREDETERMINED DATA OF LIVING TISSUE

[75] Inventor: Takuo Aoyagi, Tokyo, Japan

[73] Assignee: Nihon Kohden Corporation, Tokyo, Japan

[21] Appl. No.: 14,269

[22] Filed: Feb. 5, 1993

[30] Foreign Application Priority Data

Feb. 6, 1992 [JP] Japan ................... 4-021204
Mar. 19, 1992 [JP] Japan ................... 4-063307
Mar. 19, 1992 [JP] Japan ................... 4-063308

[51] Int. Cl.⁶ .............................. A61B 5/00
[52] U.S. Cl. ................... 128/633; 128/664; 128/665; 356/41
[58] Field of Search ............... 128/633–635, 128/664–667; 356/39–41

[56] References Cited

U.S. PATENT DOCUMENTS

4,586,513  5/1986  Hamaguri ................ 128/633
4,819,752  4/1989  Zelin ........................ 128/633

Primary Examiner—Angela D. Sykes
Attorney, Agent, or Firm—Sughrue, Mion, Zinn, Macpeak & Seas

[57] ABSTRACT

Disclosed is an apparatus for measuring a predetermined data of a living tissue, such as an oxygen saturation, a dye dilution curve and level of hemoglobin. The apparatus has an illumination intensity computing and storing circuit that stores the intensities of light components emitted from a three-wavelength light source assembly, and a computing circuit that calculates the intensity ratios of illuminating light from the intensity data stored in the circuit. The circuit determines the predetermined data of blood on the basis of the calculated intensity ratios and the intensities of light transmitted through a living tissue under assay, and it displays the predetermined data on display unit. The apparatus is capable of measuring the predetermined data without relying upon pulsations that occur in the subject.

10 Claims, 5 Drawing Sheets

APPARATUS FOR MEASURING PREDETERMINED DATA OF LIVING TISSUE

BACKGROUND OF THE INVENTION

This invention relate to apparatus for measuring a predetermined data of a living tissue which is applied to an apparatus for measuring an oxygen saturation, an apparatus for measuring a dye dilution curve, as well as an apparatus for measuring the level of hemoglobin in tissues.

Apparatuses of the type contemplated by the present invention have heretofore been operated under the principle of a "pulse oximeter", namely, by using pulsations that occur in living tissues containing blood. However, this method of measurement involves difficulty and does not insure correct results when the pulsation is low. Further, the method is susceptible to subject movement since it relies upon small changes in signal.

Another apparatus used today is one that performs measurement with reference made to light that has been transmitted through an ischemic earlobe. However, this apparatus not only uses a complicated mechanism for causing ischemia in the earlobe but also requires great skill in performing that operation. Furthermore, errors can occur on account of such factors as tissue distortion during the step of causing ischemia.

Thus, the conventional apparatuses have had various problems including the failure to provide correct results with low pulsation, high susceptibility to subject movement, and the inherent need to employ cumbersome and, hence, error-prone operations of measurement.

The level of hemoglobin or blood in living tissue is an effective index for evaluating whether circulation in the tissue of interest is successful or not. If blood supply to the brain is impaired by increased intracerebral pressure, the brain tissue can be damaged irreversibly. In order to prevent this phenomenon, it is important to perform continuous monitoring of the level of hemoglobin or blood in tissue. However, no apparatuses have so far been available that yield quantitative values in the measurement of hemoglobin and blood levels in tissue.

SUMMARY OF THE INVENTION

The present invention has been accomplished under these circumstances and has as an object providing an apparatus for measuring a predetermined data of living tissue that is capable of correct measurement irrespective of the intensity of pulsations in subject, that is less susceptible to subject movement and which yet is simple to use, causing reduced errors in measurement.

Another object of the present invention is to provide an apparatus for measuring a concentration of a pigment that has the features just described above.

A further object of the present invention is to provide an apparatus capable of measuring the level of hemoglobin or blood in tissue in a quantitative manner.

According to the first aspect of the present invention, the apparatus for measuring a predetermined data of living tissue comprises an illuminating device for illuminating a blood-containing tissue with light emitting at three wavelengths, a photoelectric transducing device for receiving light transmitted through the tissue and which then converts it to electric signals, a memory device for storing the intensities of illuminating light emitting at three wavelengths, and a computing device for computing said predetermined data of blood on the basis of the output from said photoelectric transducing device and said intensities of illuminating light stored in said memory device.

In the first aspect of the present invention, the computing means calculates the ratios between the intensities of illuminating light emitting at three wavelengths on the basis of those intensities stored in the memory device.

In the first aspect of the present invention, the memory device is replaced by a memory device for storing the ratios between the intensities of illuminating light emitting at three wavelengths and that the computing device performs the calculation on the basis of the stored ratios.

In the first aspect of the present invention, the illumination means has a scattering plate, through which the light emitting at three wavelengths is caused to pass before illuminating the tissue.

In the first aspect of the present invention, the predetermined data include an oxygen saturation, the level of hemoglobin or blood in tissue and a pigment concentration.

According to the present invention, the computing device performs its function using not only the intensities of illuminating light emitting at three wavelengths that have been stored in the memory means but also the signals produced by photoelectric conversion of the light at three wavelengths that has passed through the tissue.

According to the present invention, the computing device first calculates the ratios between the intensities of illuminating light and then calculates the oxygen saturation or the pigment concentration using the thus calculated ratios in intensity.

According to the present invention, the memory device is preloaded with the ratios between the intensities of illuminating light emitting at three wavelenghts and the oxygen saturation computing device performs its function using those ratios in intensity.

According to the present invention, the light emitted from the illumination device passes through the scattering plate and the resulting scattered light is applied to the tissue. Hence, the absorbance rate of light at a specific site in the tissue is the same irrespective of whether it is shallow or deep, whereby correct results of measurement are attained.

According to the present invention, intensities of illuminating light emitting at three wavelengths are provided by measuring for light that has been transmitted through the light attenuating plate having predetermined attenuation characteristics. Hence, the light to be measured with the apparatus under consideration is weaker than what is to be measured by the direct method. Therefore, the photoelectric transducing device to be used in intensity measurement suffices to be the same as what is used to perform conversion to electric signals on the light that has passed through the living tissue. In other words, a single photoelectric transducing device is sufficient for measuring both the intensities of illuminating light and those of light that has passed through the tissue.

According to second aspect of the present invention, an apparatus for measuring data of living tissue comprises light generating device for generating light having at least two wavelengths, a photoelectric transducing device that is spaced from said light generating means and which, upon receiving the light emitted from said light generating device, converts it to electric signals, a memory device for storing the intensity ratio of the light components at respective wavelengths that are emitted from said light generating device, and an intra-tissue hemoglobin computing device which, when a living tissue is inserted in the space between said light generating device and said photoelectric transducing device, performs predetermined calculations on the basis of both the output from said photoelectric transducing device and the intensity ratio stored in said memory device thereby determining the level of said data.

In the second aspect of the present invention, said apparatus further includes an intensity ratio computing device which, on the basis of the output from the photoelectric transducing device, calculates the intensity ratio of the light components at respective wavelengths that are emitted from said light generating device, whereas the memory device stores the intensity ratio thus calculated by the intensity ratio computing device.

In the second aspect of the present invention, said apparatus further includes a light attenuating plate having known attenuation characteristics and the intensity ratio computing device for calculating the intensity ratio on the basis of the output from the photoelectric transducing device as produced when the light attenuating plate is inserted between the light generating device and the photoelectric transducing device.

In the second aspect of the present invention, the light generating device has a scattering plate, through which the light components of the respective wavelengths are caused to pass before they are received by the photoelectric transducing device.

In the second aspect of the present invention, the predetermined data include the level of the hemoglobin or blood.

According to the present invention, the photoelectric transducing device, when a living tissue is inserted in the space between the light generating device and the transducing device, converts to electric signals the light that has been transmitted through the living organism. On the basis of these electric signals and the intensity ratio stored in the memory device, the intra-tissue hemoglobin computing device performs predetermined calculations so as to determine the level of either hemoglobin or blood in the tissue.

DETAILED DESCRIPTION OF THE PREFERRED EMBODIMENTS

Figure 1:
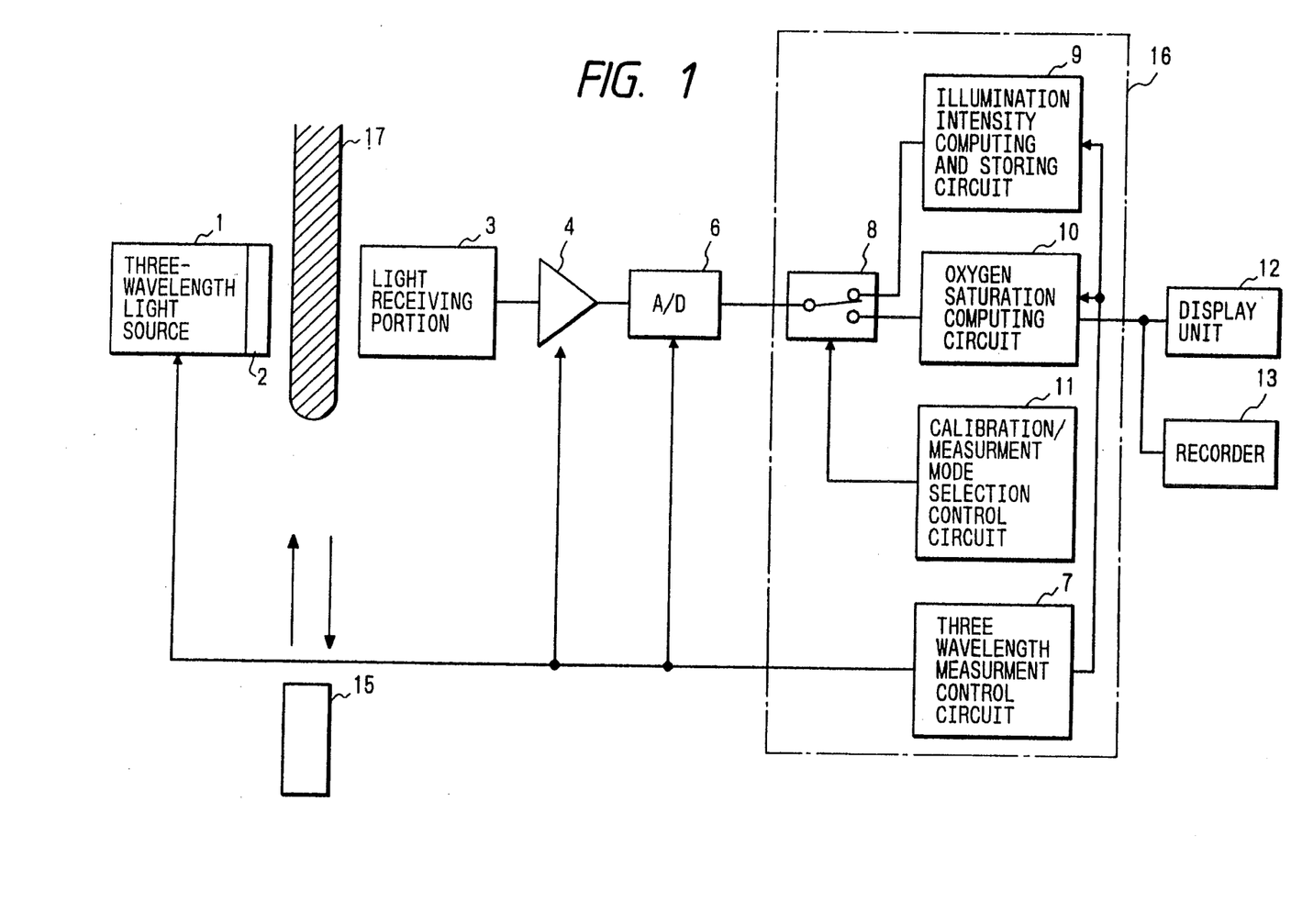
FIG. 1 is a block diagram showing the overall composition of a system in which the concept of the present invention is applied to a non-invasive oximeter.

FIG. 1 is a block diagram showing the overall composition of a system in which the concept of the present invention is applied to a non-invasive oximeter. Before going into details of the system its operating principle is first described below.

The light to be used in the system emits at three wavelengths, 805 nm ($\lambda_1$), 890 nm ($\lambda_2$) and 650 nm ($\lambda_3$), and the respective wavelengths have the following characteristics:

$\lambda_1$: The extinction coefficient of hemoglobin is independent of the oxygen saturation;

$\lambda_2$: The extinction coefficient of hemoglobin is not largely dependent on the oxygen saturation; and $\lambda_3$: The extinction coefficient of hemoglobin is highly dependent on the oxygen saturation.

It should be noted that whenever suffixes 1, 2 and 3 are added to symbols in the following description, the light components having wavelengths $\lambda_1$, $\lambda_2$ and $\lambda_3$ are meant.

It is already known both theoretically (by Schuster's theory) and empirically that the absorbance, $A_1$, $A_2$ and $A_3$, of the light components at three wavelengths that have passed through a living tissue containing blood are expressed as follows if the incident or emitted light is appropriate scattered light:

$$A_1 \equiv \log(Ie_1/It_1) \qquad (1)$$
$$= \{Eh_1Hb(Eh_1Hb + G)\}^{\frac{1}{2}}Db + ZtDt$$

$$A_2 \equiv \log(Ie_2/It_2) \qquad (2)$$
$$= \{Eh_2Hb(Eh_2Hb + G)\}^{\frac{1}{2}}Db + ZtDt$$

$$A_3 \equiv \log(Ie_3/It_3) \qquad (3)$$
$$= \{Eh_3Hb(Eh_3Hb + G)\}^{\frac{1}{2}}Db + ZtDt$$

where

Ie: the intensity (energy per unit area) of emitted light

It: the intensity (energy per unit area) of transmitted light

Eh: the extinction coefficient of hemoglobin

Hb: the concentration of hemoglobin in blood

G: the scattering constant of blood

Db: the effective thickness of the blood layer

Zt: the absorbance rate of light by a blood-free tissue (called "pure tissue"), or the absorbance divided by the thickness of the pure tissue, which is constant at any of the wavelengths $\lambda_1$, $\lambda_2$ and $\lambda_3$ Dt: the thickness of the pure tissue In eqs. (1) to (3), the symbol "$\equiv$" is definition that the right and left sides of an identical equation are identical to each other.

The "appropriate scattered light" as the incident or emitted light may be explained as follows. Parallel beams of light incident on a scattering body will be scattered as they propagate through it and in an area of a certain depth, the degree of their scattering will reach the value inherent in the body. Hence, when the scattering body is illuminated with straight travelling light, the absorbance rate will differ in a shallow and a deep area. However, if the incident or emitted light is scattered by means of a plate having the same scattering property as the living tissue to be examined, the absorbance rate of light will become uniform throughout the tissue. Thus, by providing such a scattering plate on the surface of the assembly of light-emitting diodes, the "scattered light appropriate as the emitted light" can be produced.

Let us define $\psi$, or the ratio between two differential degrees of light attenuation, $A_3 - A_2$ and $A_1 - A_2$:

$$\psi \equiv (A_3 - A_2)/(A_1 - A_2) \qquad (4)$$

Eq. (4) can be expressed by eqs. (1), (2) and (3) as follows:

$$\begin{aligned}\psi &= (A_3 - A_2)/(A_1 - A_2) \\ &= \log[(Ie_3/It_3)/(Ie_2/It_2)]/\log[(Ie_1/It_1)/(Ie_2/It_2))] \\ &= \{\log(Ie_3/Ie_2) - \log(It_3/It_2)\}/\{\log(Ie_1/Ie_2) - \log(It_1/It_2)\}\end{aligned} \qquad (4a)$$

where $Ie_3/Ie_2$ and $Ie_1/Ie_2$ are two ratios between the intensities of emitted light.

The intensity of emitted illuminating light per se is greatly influenced by conditions of measurement such as the distance between the light source and the light-receiving portion but the ratios between the intensities of light emitting at three wavelengths are not.

The ratios between the intensities of illuminating light can be determined by the following method. Even if one wants to measure illuminating light directly, its illuminance may be so high that it is sometimes difficult to achieve the intended measurement in the portion that is to receive the transmitted light. Under the circumstances, the illuminating light is allowed to pass through a light attenuating plate and attenuate light by uniform degree over the operating wavelength range, and the ratios between the intensities of illuminating light at three wavelengths are calculated for the transmitted light.

With the two intensity ratios of illuminating light, $Ie_3/Ie_2$ and $Ie_1/Ie_2$, being thus determined, the intensities of three components of the transmitted light, $It_1$, $It_2$ and $It_3$, are measured and by substituting the relevant values in eq. (4a), $\psi$ can be readily computed.

Looking at eqs. (1), (2) and (3), $\psi$ can also be expressed as follows:

$$\psi = [\{Eh_3Hb(Eh_3Hb+G)\}^{\frac{1}{2}} - \{Eh_2Hb(Eh_2Hb+G)\}^{\frac{1}{2}}]/[\{Eh_1Hb(Eh_1Hb+G)\}^{\frac{1}{2}} - \{Eh_2Hb(Eh_2Hb+G)\}^{\frac{1}{2}}] \qquad (5)$$

If the concentration of hemoglobin is not abnormally high, namely in the case where Hb<20 (g/dL), G may as well be considered to be equal to FHb (F is a constant, which is hereunder named the "scattering coefficient" for convenience sake). Substituting G=FHb in eq. (5), the latter can be rewritten as:

$$\psi = [\{Eh_3(Eh_3F)\}^{\frac{1}{2}} - \{Eh_2(Eh_2+F)\}^{\frac{1}{2}}]/[\{Eh_1(Eh_1+F)\}^{\frac{1}{2}} - \{Eh_2(Eh_2+F)\}^{\frac{1}{2}}] \qquad (6)$$

The following equations are valid in consideration of the light absorbing characteristics of hemoglobin with respect to wavelength:

$$\begin{aligned}Eh_1 &= Eo_1 & (7)\\ Eh_2 &= Eo_2 & (8)\\ Eh_3 &= SEo_3 + (1-S)Er_3 & (9)\\ &= S(Eo_3 - Er_3) + Er_3 \\ &= Er_3 - S\Delta E_3\end{aligned}$$

where
S: the oxygen saturation
Eo: the extinction coefficient of oxy-hemoglobin
Er: the extinction coefficient of reduced hemoglobin $$\Delta E_3 = Er_3 - Eo_3$$

Looking at eqs. (7), (8) and (9), eq. (6) can be rewritten as:

$$\psi = [\{Eh_3 - S\Delta E_3)((Eh_3 - S\Delta E_3)+F)\}^{\frac{1}{2}} - \{Eo_2(Eo_2+F)\}^{\frac{1}{2}}]/[\{Eo_1(Eo_1+F)\}^{\frac{1}{2}} - (Eo_2(Eo_2+F)\}^{\frac{1}{2}}] \qquad (10)$$

If $\{Eo_1(Eo_1+F)\}^{\frac{1}{2}} \equiv Eb_1$ and $\{Eo_2(Eo_2+F)\}^{\frac{1}{2}} \equiv Eb_2$, eq. (10) is rewritten as:

$$\psi = [\{(Eh_3-S\Delta E_3)(Er_3-S\Delta E_3+F)\}^{\frac{1}{2}} - Eb_2]/(Eb_1-Eb_2) \qquad (11)$$

Solving eq. (11) for the oxygen saturation S we obtain:

$$S = \{-B \pm (B^2 - 4AC)^{\frac{1}{2}}\}/2A \qquad (12)$$

where A, B and C are defined as follows:

$$A \equiv \Delta E_3^2$$

$$B \equiv -\Delta E_3 (2Er_3 + F)$$

$$C \equiv Er_3(Er_3+F) - [\psi(Z_1-Z_2)+Z_2]^2$$

In this way, the oxygen saturation can be determined by computation.

The construction of the apparatus shown in FIG. 1 is described below. A three-wavelength light source assembly indicated by 1 has three light-emitting diodes that emit light at wavelengths of 805 nm, 890 nm and 650 nm, and a scattering plate 2 through which the light from the diodes will pass. The plate 2 has a scattering property close to that of the living tissue to be assayed.

A light-receiving portion 3 is a sensor that is spaced from the light source assembly 1 and by which the light from the light source assembly is converted to electric signals. An amplifier 4 is a circuit that amplifies the electric signals produced from the light-receiving portion 3. An A/D converter 6 is a circuit by which the output signals from the amplifier 4 are converted to digital signals. A three-wavelength measurement control circuit 7 outputs signals that allow the three LEDs in the light source assembly 1 to be actuated in succession to emit light at predetermined timings. The signals from the control circuit 7 are also supplied to the amplifier 4, A/D converter 6, illumination intensity computing and storing circuit 9, and oxygen saturation computing circuit 10.

A selection switch 8 is operated in such a way that the output from the A/D converter 6 is selectively supplied to either the illumination intensity computing and storing circuit 9 or the oxygen saturation computing circuit 10. The selecting operation of the switch 8 is controlled by a calibration/measurement mode selection control circuit 11.

A display unit 12 and a recorder 13 will respectively display and record the result of computation by the oxygen saturation computing circuit 10.

The illumination intensity computing and storing circuit 9 performs predetermined calculations using the output from the A/D converter 6 and stores the result of those calculations. The oxygen saturation computing circuit 10 performs predetermined calculations on the basis of both the output from the A/D converter 6 and the contents stored in the illumination intensity computing and storing circuit 9 and outputs the result of those calculations to both the display unit 12 and the recorder 13.

The procedure of operating the system shown in FIG. 1 is next described below. First, the operator provides a light attenuating plate 15 between the three-wavelength light source assembly 1 and the light-receiving portion 3. He then activates the calibration/measurement mode selection control circuit 11 and places the switch 8 in such a position that the A/D converter 6 is connected to the illumination intensity computing and storing circuit 9. Subsequently, the operator causes the three-wavelength measurement control circuit 7 to start the control mode, whereupon the three-wavelength light source assembly 1, illumination intensity computing and storing means 9, oxygen saturation computing circuit 10 and A/D converter 6 are controlled by control signals being supplied from the three-wavelength measurement control circuit 7. Stated more specifically, the light source assembly 1 will emit light at the wavelengths $\lambda_1$ (805 nm), $\lambda_2$ (890 nm) and $\lambda_3$ (650 nm) at predetermined intervals. The individual components of the emitted light pass through the attenuating plate 15 and are incident on the light-receiving portion 3, where they are converted to electric signals. The amplifier 4, A/D converter 6 and the illumination intensity computing and storing circuit 9 will operate in synchronism with the timing at which the three-wavelength light source assembly is lit. The signals thus supplied to the illumination intensity computing and storing means 9 correspond to $Ie_1$, $Ie_2$ and $Ie_3$ in eq. (4a), which are to be stored by the illumination intensity computing and storing means 9.

In the next step, the operator removes the plate 15 and in its stead provides a living tissue of interest 17 (e.g. a finger or earlobe) between the three-wavelength light source assembly 1 and the light-receiving portion 3. He then activates the calibration/measurement mode selection control circuit 11 and places the switch 8 in such a position that the A/D converter 6 is connected to the oxygen saturation computing circuit 10. Subsequently, the operator causes the three-wavelength measurement control circuit 7 to start the control mode. As in the case of measuring the intensity of illuminating light using the attenuation plate 15, the A/D converter 6 supplies the oxygen saturation computing circuit 10 with output signals that correspond to $It_1$, $It_2$ and $It_3$ in eq. (4a). The oxygen saturation computing circuit 10 computes two ratios of illumination intensity, $Ie_3/Ie_2$ and $Ie_1/Ie_2$, on the basis of the output from the illumination intensity computing and storing circuit 9. The intensity ratios of both transmitted and emitted (illuminating) light are substituted into eq. (4a) to determine $\psi$. Then, the oxygen saturation computing circuit 10 substitutes the determine $\psi$ into eq. (12) to calculate the oxygen saturation S ($\psi$ is included in C in eq. (12)). The thus determined oxygen saturation S is displayed on the display unit 12 and recorded by the recorder 13.

In the embodiment under consideration, the light attenuating plate 15 is used to measure the intensity of emitted illuminating light and, therefore, the measuring instrument may be the same as what is used to measure the intensity of light that has been transmitted through the living tissue 17. The plate 15 desirably causes light to be attenuated by the same degree at each of the operating wavelengths of the light source assembly; however, even if the plate causes different degrees of attenuating, there is no problem at all if the differences are known and can be corrected by the means of computing the intensity ratio of emitted light. In the described case, the light components of three wavelengths are successively applied to the attenuating plate or living tissue but, if desired, they may be applied at a time and the respective components of transmitted light are simultaneously received from photoelectric conversion and, on the basis of output signals, $Ie_3/Ie_2$, $Ie_2/Ie_1$, $It_3/It_2$ and $It_1/It_2$ are directly determined and stored for use in subsequent calculation by eq. (4a).

In the embodiment under consideration, the light emitted from the three-wavelength light source assembly 1 has already passed through the scattering plate and, hence, there is no possibility that the absorbance rate of light varies in a shallow and a deep area of the living tissue under examination.

The embodiment has another advantage in that using the intensity ratio of emitted light, it is less subjected to the effect of measuring conditions.

A further advantage of the embodiment is that being capable of measuring and storing the intensity of illumination at a suitable time, it is by no means susceptible to the adverse effects of aging or fouling of the light-emitting portion.

As is clear from eq. (8), $Eh_2$ is defined by approximation in the embodiment under consideration but this causes no error if the oxygen saturation 5 is 1 (100%). As the oxygen saturation decreases, the error will increase but this does not cause any serious effect since the permissible error is great at lower levels of oxygen saturation.

Instead of approximation by eq. (8), $Eh_2$ may be expressed more correctly as follows:

$$Eh_2 = SEo_2 + (1 - S)Er_2 \quad (8a)$$
$$= S(Eo_2 - Er_2) + Er_2$$
$$= Er_2 - S\Delta E_2$$

Substituting this eq. (8a) as well as eqs. (7) and (9) into eq. (6), we obtain:

$$\psi = [(Er_3 - S\Delta E_3)(Er_3 - S\Delta E_3 + F)]^{\frac{1}{2}} - [\{(Er_2 - S\Delta E_2) \cdot (Er_2 - S\Delta E_2 + F)\}^{\frac{1}{2}}/\{Eo_1(Eo_1 + F)\}^{1/8} - [(Er_2 - S\Delta E_2)(Er_2 - S\Delta E_2 + F)]^{\frac{1}{2}} \quad (13)$$

To take advantage of this eq. (13), one may replace the oxygen saturation computing circuit 10 by a circuit that performs the following functions: starting with unity, numerals that decrease by increments of a certain value, say, 0.01 are substituted into S on the right side of eq. (13); each of the computed values of the right side is compared with $\psi$ on the left side; when $\psi$ is exceeded, the pertinent value of S is supplied as output to the display unit 12 and the recorder 13.

In the embodiment described on the foregoing pages, various calculations and controls are performed by independent circuits but they may be implemented by a computer. On the pages that follow, description is made of a system in which the portion indicated by 16 in FIG. 1 which consists of illumination intensity computing and storing circuit 9, oxygen saturation computing circuit 10, calibration/measurement mode selection control circuit 11, three-wavelength measurement control circuit 7 and selection switch 8 is replaced by a microcomputer.

Figure 2:
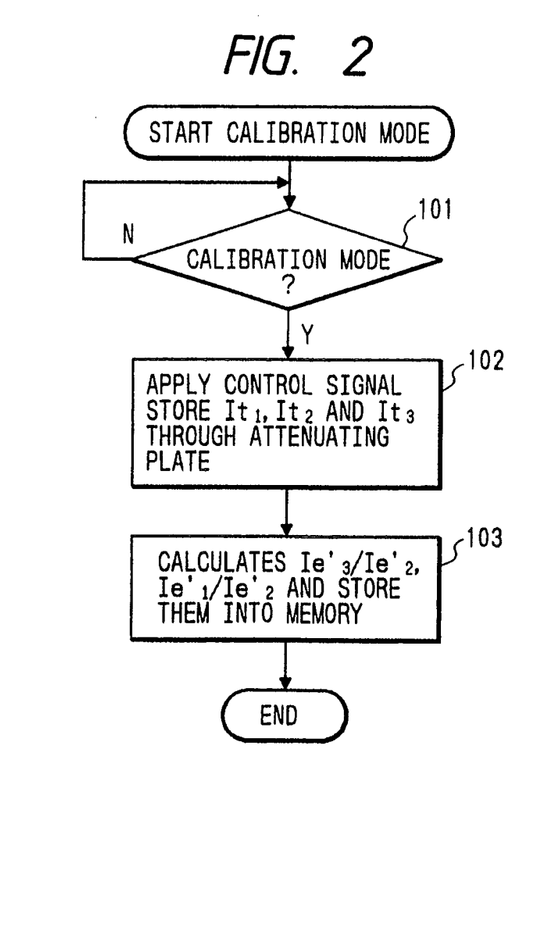
FIG. 2 is a flow charge illustrating the sequence of steps for operating the system of FIG. 1.
Figure 3:
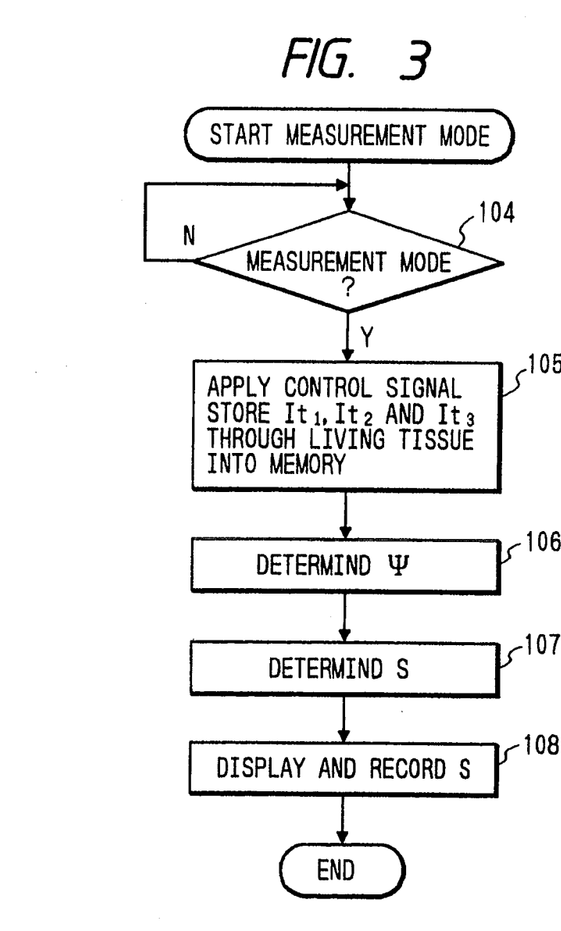
FIG. 3 is a flow charge illustrating the sequence of steps for operating the system of FIG. 1.

In this case, the microcomputer has a program to be executed in accordance with the flow charts shown in FIGS. 2 and 3. The operation of the microcomputer is now described with reference to those flow charts.

First, the microcomputer is in a standby condition until the "calibration mode" is on (step 101 in FIG. 2). The operator inserts the light attenuating plate 15 between the three-wavelength light source assembly 1 and the light-receiving portion 3 and manipulates the input means to effect changeover to the "calibration mode". The microcomputer controls the three-wavelength light source assembly 1, amplifier 4 and the A/D converter 6 to produce $Ie_1'$, $Ie_2'$ and $Ie_3'$ (as well as $It_1$, $It_2$ and $It_3$ for the light transmitted through the attenuating plate) and load them into the memory (step 102). Then, the microcomputer calculates $Ie_3'/Ie_2'$ ($=Ie_3/Ie_2$) and $Ie_1'/Ie_2'$ ($=Ie_1/Ie_2$) from $Ie_1'$, $Ie_2'$ and $Ie_3'$ and load them into the memory (step 103). Subsequently, the operator takes the attenuating plate 15 from between the three-wavelength light source assembly 1 and the light-receiving portion 3 and in its instead inserts the living tissue 17 to be assayed; then, he manipulates the input means to effect changeover to the "measurement mode" while the computer is in a standby state waiting for the changeover to the "measurement mode" to be effected (step 104 in FIG. 3). When the "measurement mode" is on, the microcomputer controls the three-wavelength light source assembly 1, amplifier 4 and A/D converter 6 to produce $It_1$, $It_2$ and $It_3$ and load them into the memory (step 105). The microcomputer then retrieves $Ie_3/Ie_2$, $Ie_1/Ie_2$, $It_1$, $It_2$ and $It_3$ from the memory and substitutes them in eq. (4a) to determine $\psi$ (step 106). The determined $\psi$ is substituted in eq. (12) to determine S (step 107), which is then displayed on the display unit 12 and recorded by the recorder 13 (step 108).

The first embodiment of the present invention eliminates the need to measure the fluctuations in transmitted light due to the pulsation of arterial blood in the living tissue under assay. This offers the advantage of providing correct results of measurement even for subjects who have low pulsations. A further advantage is that the usability of large signals permits the intended measurement to be performed with minimum effects of subject movement.

According to the first embodiment of the present invention, not only the oxygen saturation of arterial blood but also the overall value including venous blood can be measured. If compared with the value specific for arterial blood, the overall value can serve as an index for the insufficiency of oxygen supply to a particular tissue such as the brain substance. The overall value finds especially high value as an index for intracerebral oxygen supply.

We now describe the operating principle of a system in which the concept of the present invention is applied to an apparatus for measuring a dye dilution curve according to its second aspect.

The light to be used in the system emits at three wavelengths, 805 nm ($\lambda_1$), 890 nm ($\lambda_2$) and 650 nm ($\lambda_3$), and the respective wavelengths have the following characteristics:

$\lambda_1$: Not affected by the oxygen saturation but maximum light absorption by pigment occurs;

$\lambda_2$: Affected only weakly by the oxygen saturation but not affected by light absorption by pigment; and $\lambda_3$: Affected by both the oxygen saturation and the light absorption by pigment.

It should be noted that whenever suffixes 1, 2 and 3 are added to symbols in the following description, the light components having wavelengths $\lambda_1$, $\lambda_2$ and $\lambda_3$ are meant.

It is known both theoretically (by Schuster's theory) and empirically that the absorbance, $A_1$, $A_2$ and $A_3$, of the light components at three wavelengths that have passed through a living tissue containing blood are expressed as follows if the incident or emitted light is appropriate scattered light:

Before pigment injection $$A_1 = \log(Ie_1/It_1) \\ = \{Eh_1Hb(Eh_1Hb + G)\}^{\frac{1}{2}}Db + ZtDt \quad (101)$$

$$A_2 = \log(Ie_2/It_2) \\ = \{Eh_2Hb(Eh_2Hb + G)\}^{\frac{1}{2}}Db + ZtDt \quad (102)$$

$$A_3 = \log(Ie_3/It_3) \\ = \{Eh_3Hb(Eh_3Hb + G)\}^{\frac{1}{2}}Db + ZtDt \quad (103)$$

After pigment injection $$A_1 = \log(Ie_1/It_1) \\ = \{(Eh_1Hb + Ed_1Cd)(Eb_1Hb + Ed_1Cd + G)\}^{\frac{1}{2}}Db + ZtDt \quad (104)$$

$$A_2 = \log(Ie_2/It_2) \\ = \{(Eh_2Hb)(Eh_2Hb + G)\}^{\frac{1}{2}}Db + ZtDt \quad (105)$$

$$A_3 = \log(Ie_3/It_3) \\ = \{(Eh_3Hb + Ed_3Cd)(Eh_3Hb + Ed_3Cd + G)\}^{\frac{1}{2}}Db + ZtDt \quad (106)$$

where
Ie: the intensity (energy per unit area) of emitted light
It: the intensity (energy per unit area) of transmitted light
Eh: the extinction coefficient of hemoglobin
Hb: the concentration of hemoglobin in blood
G: the scattering constant of blood
Ed: The extinction coefficient of pigment
Cd: the concentration of pigment in blood
Db: the effective thickness of the blood layer
Zt: the absorbance rate of light by a blood-free tissue (called "pure tissue"), or the degree of light attenuation divided by the thickness of the pure tissue, which is constant at any of the wavelengths $\nu_1$, $\nu_2$ and $\nu_3$
Dt: the thickness of the pure tissue.

Let us define $\psi$, or the ratio between two differential degrees of light attenuation, $A_1-A_2$ and $A_3-A_2$, as follows:

$$\psi = (A_1-A_2)/(A_3-A_2) \quad (104)$$

Eq. (104) can be expanded by eqs. (101), (102) and (103) as follows:

$$\psi = (A_1 - A_2)/(A_3 - A_2) \quad (104a) \\ = \log[(Ie_1/It_1)/(Ie_2/It_2)]/\log[(Ie_3/It_3)/(Ie_2/It_2)] \\ = \{\log(Ie_1/Ie_2) - \log(It_1/It_2)\}/\{\log(Ie_3/Ie_2) - \log(It_3/It_2)\}$$

where $Ie_3/Ie_2$ and $Ie_1/Ie_2$ are two ratios between the intensities of emitted light.

The intensity of emitted illuminating light per se is greatly influenced by conditions of measurement such as the distance between the light source and the light-receiving portion but the ratios between the intensities of light emitting at three wavelengths are not.

The ratios between the intensities of illuminating light can be determined by the following method. Even if one wants to measure illuminating light directly, its illuminance may be so high that it is sometimes difficult to achieve the intended measurement in the portion that is to receive the transmitted light. Under the circumstances, the illuminating light is allowed to pass through a light attenuating plate that attenuates light by uniform degree over the operating wavelength range, and the ratios between the intensities of illuminating light at three wavelengths are calculated for the transmitted light.

With the two intensity ratios of illuminating light, $Ie_3/Ie_2$ and $Ie_1/Ie_2$, being thus determined, the intensities of three components of the transmitted light, $It_1$, $It_2$ and $It_3$, are measured and by substituting the relevant values in eq. (104a), $\psi$ can be readily computed.

Looking at eqs. (101), (102) and (103), $\psi$ before pigment injection can also be expressed as follows:

$$\psi = [\{Eh_1Hb(Eh_1Hb+G)\}^{\frac{1}{2}} - \{Eh_2Hb(Eh_2Hb+G)\}^{\frac{1}{2}}]/[\{Eh_3Hb(Eh_3Hb+G)\}^{\frac{1}{2}} - \{Eh_2Hb(Eh_2Hb+G)\}^{\frac{1}{2}}] \quad (107)$$

Looking at eqs. (104), (105) and (106), $\psi$ after pigment injection can also be expressed as follows:

$$\psi = [\{(Eh_1Hb + Eh_1Cd)(Eh_1Hb + Eh_1Cd + G)\}^{\frac{1}{2}} \cdot Db - \{Eh_2Hb(Eh_2Hb + G)\}^{\frac{1}{2}}Db]/[\{(Eh_3Hb + Ed_3Cd)(Eh_3Hb + Ed_3Cd + G)\}^{\frac{1}{2}} \cdot Db - \{Eh_2Hb(Eh_2Hb + G)\}^{\frac{1}{2}}Db] \quad (108)$$

If the concentration of hemoglobin is not abnormally high, namely in the case where Hb<20 (g/dL), G may as well be considered to be equal to FHb (F is a constant, which is hereunder named the "scattering coefficient" for convenience sake). Substituting G=FHb in eq. (107) and (108), the latter can respectively be rewritten as:

Before pigment injection
$$\psi = [\{Eh_1(Eh_1 + F)\}^{\frac{1}{2}} - \{Eh_2(Eh_2 + F)\}^{\frac{1}{2}}]/[\{Eh_3(Eh_3 + F)\}^{\frac{1}{2}} - \{Eh_2(Eh_2 + F)\}^{\frac{1}{2}}] \quad (109)$$

After pigment injection
$$\psi = [\{(Eh_1 + Ed_1Cd')(Eh_1 + Ed_1Cd' + F)\}^{\frac{1}{2}} - \{Eh_2(Eh_2 + F)\}^{\frac{1}{2}}]/[\{(Eh_3 + Ed_3Cd')(Eh_3 + Ed_3Cd' + F)\}^{\frac{1}{2}} - \{Eh_2(Eh_2 + F)\}^{\frac{1}{2}}] \quad (110)$$

where $$Cd' = Cd/Hb \quad (111)$$

If the oxygen saturation S is held to be approximate to unity, $$Eh = EoS + Er(1-S) \quad (112)$$

where
Eo: the extinction coefficient of oxyhemoglobin
Er: the extinction coefficient of reduced hemoglobin.
Hence, the following equations are valid:

$$Eh_1 = Eo_1 \quad (113)$$

$$Eh_2 = Eo_2 \quad (114)$$

$$Eh_3 = Eo_3 \quad (115)$$

According to these approximations, eq. (110) can be rewritten as:

$$\psi = [\{(Eo_1 + Ed_1Cd')(Eo_1 + Ed_1Cd' + F)\}^{\frac{1}{2}} - \{Eo_2(Eo_2 + F)\}^{\frac{1}{2}}]/[\{(Eo_3 + Ed_3Cd')(Eo_3 + Ed_3Cd' + F)\}^{\frac{1}{2}} - \{Eo_2(Eo_2 + F)\}^{\frac{1}{2}}] \quad (116)$$

Using another approximation $Ed_3=0$, eq. (116) can be rewritten as:

$$\psi = [\{(Eo_1 + Ed_1Cd')(Eo_1 + Ed_1Cd' + F)\}^{\frac{1}{2}} - \{Eo_2(Eo_2+F)\}^{\frac{1}{2}}]/[\{Eo_3(Eo_3+F)\}^{\frac{1}{2}} - \{Eo_2(Eo_2+F)\}^{\frac{1}{2}}] \quad (117)$$

If $$Z_2 = Eo_2(Eo_2 + F) \quad (118)$$

$$Z_3 = Eo_3(Eo_3 + F) \quad (119)$$

eq. (117) is rewritten as:

$$\{(Eo_1 + Ed_1Cd')(Eo_1 + Ed_1Cd' + F)\}^{\frac{1}{2}} - Z_2 = \psi(Z_3 - Z_2) \quad (120)$$

Eq. (120) can be rearranged as:

$$Ed_1^2Cd'^2 + Ed_1Cd'(2Eo_1+F) + Eo_1(Eo_1+F) - \{\psi(Z_3-Z_2)+Z_2\}^2 = 0 \quad (121)$$

Solving eq. (12) for Cd', we obtain:

$$Cd' = \{-B + (B^2 - 4AC)^{\frac{1}{2}}\}/2A \quad (122)$$

where A, B and C are defined as follows:

$$A = Ed_1^2: \text{constant} \quad (123)$$

$$B = Ed_1(2Eo_1 + F): \text{constant} \quad (124)$$

$$C = Eo_1(Eo_1 + F) - \{\psi(Z_3 - Z_2) + Z_2\}^2 \quad (125)$$

If Cd' before pigment injection is written as $Cd_0'$, then the concentration of pigment in blood, D, can be expressed as:

$$D = (Cd' - Cd_0')Hb \quad (126)$$

Hence, if $\psi$ before pigment injection is written as $\psi_0$, eq. (125) dictates that $C_0$, or C before pigment injection, is:

$$C_0 = Eo_1(Eo_1 + F) - \{\psi_0(Z_3 - Z_2) + Z_2\}^2 \quad (127)$$

Hence, eq. (122) dictates:

$$Cd_0' = \{-B + (B^2 - 4AC_0)^{\frac{1}{2}}\}/2A \quad (128)$$

Looking at eq. (126), one can see that the concentration of pigment in blood, D, is expressed as:

$$D = +\{(B^2 - 4AC)^{\frac{1}{2}} - (B^2 - 4AC_0)^{\frac{1}{2}}\}Hb/2A \quad (129)$$

The construction of an apparatus that is operated by the principle described on the preceding pages is explained below with reference to FIG. 4. A three-wavelength light source assembly indicated by 201 has three light-emitting diodes that emit light at wavelengths of 805 nm, 890 nm and 650 nm, and a scattering plate 202 through which the light from the diodes will pass. The plate 202 has a scattering property close to that of the living tissue to be assayed.

A light-receiving portion 203 is a sensor that is spaced from the light source assembly 201 and by which the light from the light source assembly is converted to electric signals. An amplifier 204 is a circuit that amplifies the electric signals produced from the light-receiving portion 203. An A/D converter 206 is a circuit by which the output signals from the amplifier 204 are converted to digital signals. A three-wavelength measurement control circuit 207 outputs signals that allow the three LEDs in the light source assembly 201 to be actuated in succession to emit light at predetermined timings. The signals from the control circuit 207 are also supplied to the amplifier 204, A/D converter 206, memory circuit 209A and attenuation ratio computing circuit 210. The memory circuit 209A stores the intensities of signals that are supplied from the A/D converter 206 and which correspond to the light components of wavelengths $\lambda_1$, $\lambda_2$ and $\lambda_3$, respectively. An intensity ratio computing and storing circuit 209B computes and stores the ratios between two intensities as stored in the memory circuit 209A. The attenuation ratio computing circuit 210 performs predetermined calculations both on the basis of the signals corresponding to the light components of $\lambda_1$, $\lambda_2$ and $\lambda_3$, respectively, which are supplied from the A/D converter 206 and on the basis of the intensity ratios stored in the intensity ratio computing and storing circuit 209B.

A selection switch 208 is operated in such a way that the output from the A/D converter 206 is selectively supplied to either the memory circuit 209A or the attenuation ratio computing circuit 210. A calibration/measurement mode selection control circuit 211 controls the selecting operation of the switch 208.

A memory circuit 214 stores the results of the first calculation performed following the placement of switch 208 in such a position that the A/D converter is connected to the attenuation ratio computing circuit 210. A memory circuit 216 stores the concentration of hemoglobin Hb when it is supplied. A pigment concentration computing circuit 218 determines the concentration of pigment in blood by performing predetermined calculations on the basis of both the result of calculation by the attenuation ratio computing circuit 210 and the values stored in memory circuits 214 and 216.

A display unit 212 and a recorder 213 will respectively display and record the result of computation by the pigment concentration computing circuit 218.

Figure 4:
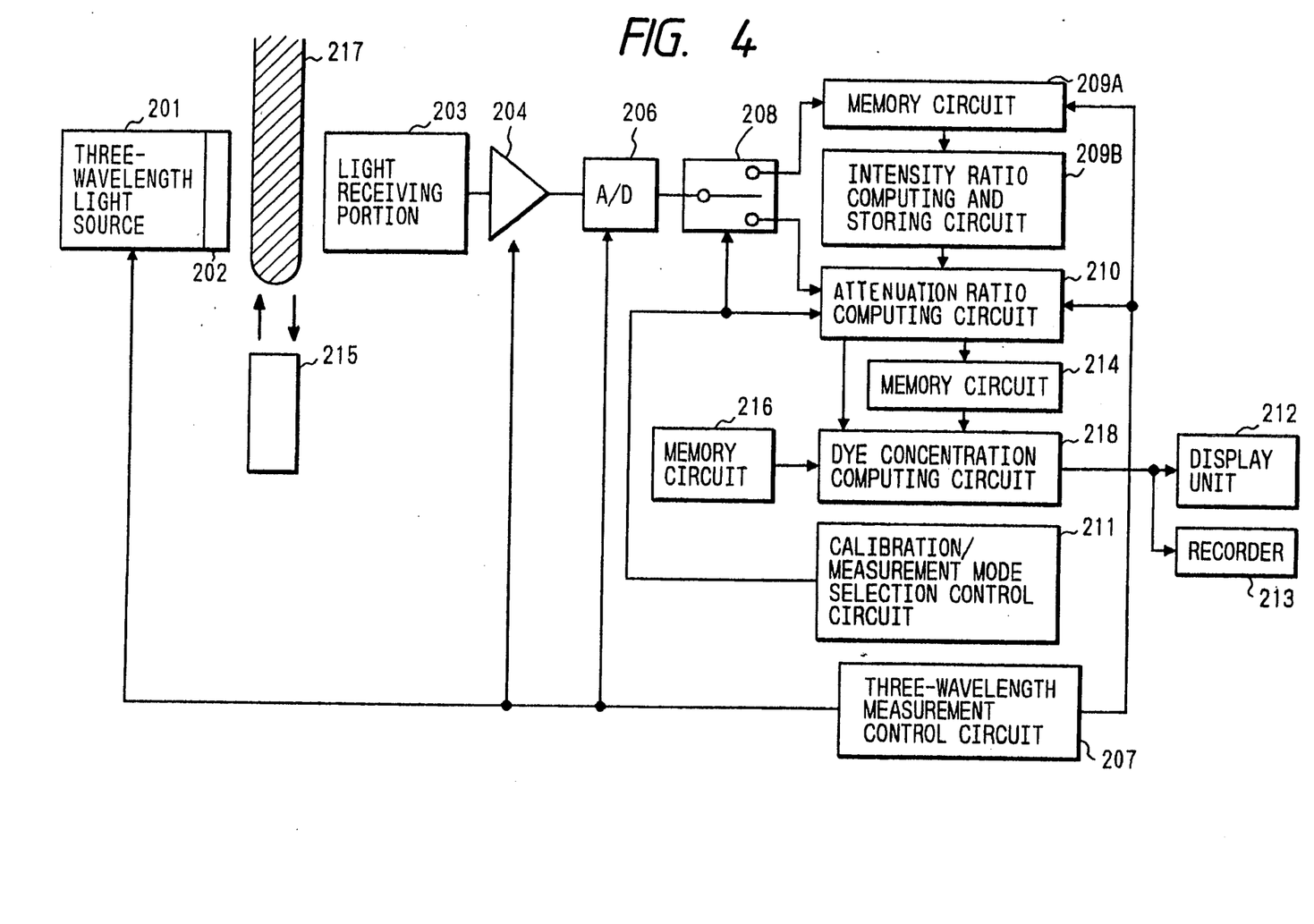
FIG. 4 is a block diagram showing the overall composition of a system in which the concept of the present invention is applied to an apparatus for measuring a concentration of a pigment.

The procedure of operating the system shown in FIG. 4 is next described below. First, the operator provides a light attenuating plate 215 between the three-wavelength light source assembly 201 and the light-receiving portion 203. He then activates the calibration/measurement mode selection control circuit 211 and places the switch 208 in such a position that the A/D converter 206 is connected to the memory circuit 209A. Subsequently, the operator causes the three-wavelength measurement control circuit 207 to start the control mode, whereupon the three-wavelength light source assembly 201, memory circuit 209A, attenuation ratio computing circuit 210 and A/D converter 206 are controlled by control signals being supplied from the three-wavelength measurement control circuit 207. Stated more specifically, the light source assembly 201 will emit light at three wavelengths $\lambda_1$ (805 nm), $\lambda_2$ (890 nm) and $\lambda_3$ (650 nm) at predetermined intervals. The individual components of the emitted light pass through the attenuating plate 215 and are incident on the light-receiving portion 203, where they are converted to electric signals. The amplifier 204, A/D converter 206 and the memory circuit 209A will operate in synchronism with the timing at which the three-wavelength light source assembly is lit. The signals thus supplied to the memory circuit 209A correspond to $Ie_1$, $Ie_2$ and $Ie_3$ in eq. (104a), which are to be stored by the memory circuit 209A. The intensity ratio computing and storing circuit 209B computes $Ie_3/Ie_2$ and $Ie_1/Ie_2$ from the contents of the memory circuit 209A and stores them.

In the next place, the operator removes the plate 215 and in its stead provides a living tissue 217 of interest (e.g. a finger or earlobe) between the three-wavelength light source assembly 201 and the light-receiving portion 203. He then activates the calibration/measurement mode selection control circuit 211 and places the switch 208 in such a position that the A/D converter 206 is connected to the attenuation ratio computing circuit 210. Subsequently, the operator causes the three-wavelength measurement control circuit 207 to start the control mode. As in the case of measuring the intensity of illuminating light using the attenuation plate 215, the A/D converter 206 supplies the attenuation ratio computing circuit 210 with output signals that correspond to $It_1$, $It_2$ and $It_3$ in eq. (104a).

The attenuation ratio computing circuit 210 computes $\psi$ by substituting the following five parameters in eq. (104a): $Ie_1/Ie_2$ and $Ie_3/Ie_2$ stored in the intensity ratio computing and storing circuit 209B and $It_1$, $It_2$ and $It_3$ supplied from the A/D converter 206. The three-wavelength measurement control circuit 207 causes the three-wavelength light source assembly 201 to repeat cyclically the successive emission of light at three wavelengths.

The memory circuit 214 stores $\psi_0$, namely, the value of $\psi$ that is first calculated out by the attenuation ratio computing circuit 210 following the placement of switch 208 in such a position that the A/D converter 206 is connected to that circuit 210.

The pigment concentration computing circuit 215 substitutes into eq. (129) the value of $\psi_0$ stored in memory circuit 214, the value of Hb stored in memory circuit 216 and the value of $\psi$ supplied from attenuation ratio computing circuit 210 ($\psi_0$ is included in Co in eq. (12) and $\psi$ is included in C in the same equation), whereby the concentration of pigment in blood, D, is determined.

Thus, the light components of three wavelengths are applied to the living tissue 217 successively and repeatedly, and the pigment concentration computing circuit 215 performs the necessary calculation on the occurrence of each application of light and the result is delivered to both the display unit 212 and the recorder 213. If a predetermined pigment is injected into the blood of the living tissue 217 after the switch 208 is placed in such a position that the A/D converter 206 is connected to the attenuation ratio computing circuit 210, the time profile of the pigment concentration D, namely, the dye dilution curve, is displayed on the display unit 212 and recorded by the recorder 213.

In this embodiment under consideration, the light attenuating plate 215 is used to measure the intensity of emitted illuminating light and, therefore, the measuring instrument may be the same as what is used to measure the intensity of light that has been transmitted through the living tissue 217. The plate 215 desirably causes light to be attenuated by the same degree at each of the operating wavelengths of the light source assembly; however, even if the plate causes different degrees of attenuating, there is no problem at all if the differences are known and can be corrected by the means of computing the intensity ratio of emitted light. In the described case, the light components of three wavelengths are successively applied to the attenuating plate or living tissue but, if desired, they may be applied at a time and the respective components of transmitted light are simultaneously received for photoelectric conversion and, on the basis of output signals, $Ie_3/Ie_2$, $Ie_2/Ie_1$, $It_3/It_2$ and $It_1/It_2$ are directly determined and stored for use in subsequent calculation by eq. (104a). In another modification, the light components of three wavelengths may be generated alternately at very short intervals and received by a means that reproduces the signals representing the respective wavelengths as separate entities. The result of this modification is the same as what is achieved by processing the light components of three wavelengths that have been generated almost simultaneously.

In the second embodiment under consideration, the light emitted from the three-wavelength light source assembly 201 has already passed through the scattering plate and, hence, there is no possibility that the absorbance rate of light varies in a shallow and a deep area of the living tissue under examination.

The second embodiment has another advantage in that using the intensity ratio of emitted light, it is less subjected to the effect of measuring conditions. A further advantage of the embodiment is that being capable of measuring and storing the intensity of illumination at a suitable time, it is by no means susceptible to the adverse effects of aging or fouling of the light-emitting portion.

In the second embodiment, the pigment concentration computing circuit 215 uses eq. (129) which is derived by adopting the approximation $Ed_3=0$. If desired, the more correct approach can be taken and one may replace the pigment concentration computing circuit 215 by a circuit that performs the following functions: starting with zero, numerals that increase by increments of a predetermined value are substituted into $Cd'$ on the right side of eq. (116); each of the computed values of the right side is compared with $\psi$ on the left side; when $\psi$ is exceeded, the pertinent value of $Cd'$ is supplied as output.

In the second embodiment described on the foregoing pages, various calculations and controls are performed by independent circuits but they may be implemented by a computer.

The second embodiment of the present invention offers the advantage of providing correct results of measurement even for subjects who have low pulsations. A further advantage is that the apparatus for measurement is less susceptible to the effect of subject movement and yet it is simple to use causing only small errors in measurement.

Let us now describe the operating principle of a system in which the concept of the present invention is applied to an apparatus for measuring the level of hemoglobin in tissue according to its third embodiment.

If the light applied to a living tissue containing blood is appropriate scattered light, the absorbance rate of light propagating through the "pure tissue" (the blood-free portion of the tissue being assayed) is not dependent on the wavelength of the light. Schuster's theory and experimentation dictate that the following relationships are valid:

$$\log(Ie_1/It_1) = \{Eh_1Hb(Eh_1Hb + G)\}^{\frac{1}{2}}Db + ZtDt \quad (301)$$

$$\log(Ie_2/It_2) = \{Eh_2Hb(Eh_2Hb + G)\}^{\frac{1}{2}}Db + ZtDt \quad (302)$$

-continued $$\log(Ie_3/It_3) = \{Eh_3Hb(Eh_3Hb + G)\}^{\frac{1}{2}}Db + ZtDt \quad (303)$$

where
Ie: the intensity (energy per unit area) of emitted light
It: the intensity (energy per unit area) of transmitted light
Eh: the extinction coefficient of hemoglobin
Hb: the concentration of hemoglobin in blood
G: the scattering constant of blood
Db: the effective thickness of the blood layer
Zt: the absorbance rate of light by a pure tissue (=absorbance divided by the thickness of the tissue), which is constant at any wavelengths
Dt: the effective thickness of the pure tissue.

It should also be noted that suffixes 1, 2 and 3 that appear in eqs. (301), (302) and (303) and hereinafter denote three light components having different wavelengths.

If the concentration of hemoglobin is not abnormally high, namely in the case where $Hb<20$ (g/dL), G may as well be considered to be equal to FHb (F is a constant, which is hereunder named the "scattering coefficient" for convenient sake). Substituting $G=HFb$ in eqs. (301), (302) and (303), the latter can respectively be rewritten as:

$$\log(Ie_1/It_1) = \{Eh_1(Eh_1 + F)\}^{\frac{1}{2}}HbDb + ZtDt \quad (304)$$

$$\log(Ie_2/It_2) = \{Eh_2(Eh_2 + F)\}^{\frac{1}{2}}HbDb + ZtDt \quad (305)$$

$$\log(Ie_3/It_3) = \{Eh_3(Eh_3 + F)\}^{\frac{1}{2}}HbDb + ZtDt \quad (306)$$

If the intensity of light transmitted through an ischemic living tissue is written as Io, the following equation if is valid for each wavelength of interest:

$$\log (Ie_1/Io_1) = \log (Ie_2/Io_2) = \log (Ie_3/Io_3) = ZtDt \quad (307)$$

The extinction coefficient of hemoglobin, Eh, is expressed as:

$$Eh = SEo + (1-S)Er \quad (308)$$

where
S: the oxygen saturation
Eo: the extinction coefficient of oxyhemoglobin
Er: the extinction coefficient of reduced hemoglobin.

In a typical case, the three wavelengths $\lambda_1$, $\lambda_2$ and $\lambda_3$ may be set at 805 nm, 890 nm and 650 nm, respectively, and these wavelengths have the following characteristics:

$\lambda_1$: The extinction coefficient of hemoglobin is independent of the oxygen saturation, with $Eh_1 = Eo_1$;
$\lambda_2$: The extinction coefficient of hemoglobin is not largely dependent on the oxygen saturation; and
$\lambda_3$: The extinction coefficient of hemoglobin is highly dependent on the oxygen saturation.

The following values are "given" since they can be determined prior to the use of the apparatus:

$$Ie_1/Ie_2 = R_{12} \quad (309)$$

$$Ie_3/Ie_2 = R_{32} \quad (310)$$

We now describe the procedure of determining the degree of light attenuation by hemoglobin.

Case where the oxygen saturation is substantially 100%
(S=1)

Looking at eq. (308), the following approximation is reasonable:

$$Eh_1 = Eo_1$$

$$Eh_2 = Eo_2 \quad (311)$$

Then, eqs. (304) and (305) can be rewritten as:

$$\log(Ie_1/It_1) = \{Eho_1(Eho_1 + F)\}^{\frac{1}{2}} HbDb + ZtDt \quad (312)$$

$$\log(Ie_2/It_2) = \{Eho_2(Eho_2 + F)\}^{\frac{1}{2}} HbDb + ZtDt \quad (313)$$

If $$Eb_1 = \{Eo_1(Eo_1 + F)\}^{\frac{1}{2}} \quad (314)$$

$$Eb_2 = \{Eo_2(Eo_2 + F)\}^{\frac{1}{2}} \quad (315)$$

eqs. (312) and (313) are rewritten as:

$$\log(Ie_1/It_1) = Eb_1 HbDb + ZtDt \quad (316)$$

$$\log(Ie_2/It_2) = Eb_2 HbDb + ZtDt \quad (317)$$

Looking at eqs. (316) and (307), we obtain:

$$\log(Ie_1/It_1) - \log(Ie_1/Io_1) = Eb_1 HbDb \quad (318)$$

$$\log Io_1 - \log It_1 = Eb_1 HbDb$$

Looking at eqs. (317) and (307), we obtain:

$$\log(Ie_2/It_2) - \log(Ie_1/Io_1) = Eb_2 HbDb$$

$$\log(Ie_2/Ie_1)(Io_1/It_2) = Eb_2 HbDb$$

Using eq. (309), this can be rewritten as:

$$-\log R_{12} + \log Io_1 - \log It_2 = Eb_2 HbDb \quad (319)$$

Looking at eqs. (318) and (319), we obtain $$(\log Io_1 - \log It_1)/(-\log R_{12} + \log Io_1 - \log It_2) = Eb_1/Eb_2$$

Hence, $$\log Io_1 = \log It_1(\log R_{12} + \log It_2)(Eb_1/Eb_2) / (Eb_1/Eb_2 - 1) \quad (320)$$

On the right side of eq. (320), $R_{12}$, $Eb_1$ and $Eb_2$ are constants whereas $It_1$ and $It_2$ can be determined by actual measurement; hence, eq. (320) enables one to determine the intensity of light that has been transmitted through ischemic blood at wavelength $\lambda_1$.

Looking at eq. (318), the degree of light attenuation by hemoglobin is expressed as:

$$\log(Io_1/It_1) = \{Eo_1(Eo_1 + F)\}^{\frac{1}{2}} HbDb \quad (323)$$
$$= Eb_1 HbDb$$

The procedure of determining the levels of hemoglobin and blood in the tissue under assay is next described below.

(A) Hemoglobin in tissue HbDb

Rewriting eq. (323), we obtain:

$$HbDb = (\log Io_1 - \log It_1)/Eb_1 \quad (324)$$

As already mentioned in connection with eq. (320), $Io_1$ on the right side of eq. (324) can be determined by measuring $It_1$ and $It_2$ whereas $Eb_1$ is a constant. Hence, HbDb can be determined by measuring $It_1$ and $It_2$, and it is expressed in (g/dL)·cm=0.01 g/cm².

(B) Blood in tissue Db
Rewriting eq. (323), we obtain:

$$Db = (\log Io_1 - \log It_1)/Eb_1 Hb \quad (325)$$

Given the concentration of hemoglobin in blood Hb, one can determine Db, which is expressed cm.

Figure 5:
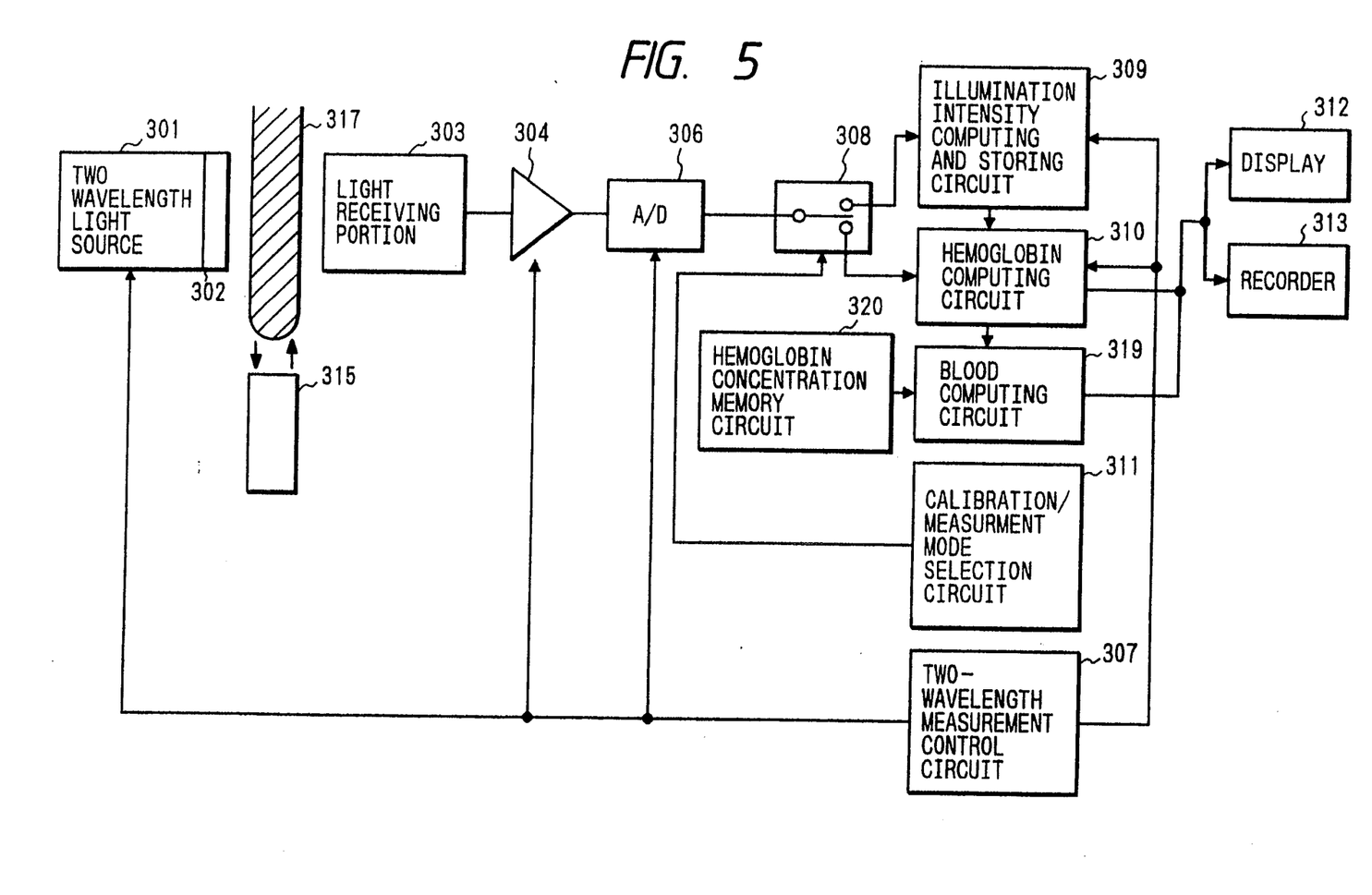
FIG. 5 is a block diagram showing the overall composition of a system in which the concept of the present invention is applied to an apparatus for measuring the level of hemoglobin in tissue.

FIG. 5 is a block diagram showing the construction of an apparatus for measuring the level of hemoglobin in tissue according to the third embodiment of the present invention. A two-wavelength light source assembly indicated by 301 has two light-emitting diodes that emit light at wavelengths 850 nm ($\lambda_1$) and 890 nm ($\lambda_2$), and a scattering plate 302 through which the light from the diodes will pass. The plate 302 has a scattering property close to that of the living tissue to be assayed.

A light-receiving portion 303 is a sensor that is spaced from the light source assembly 301 and by which the light from the light source assembly is converted to electric signals. An amplifier 304 is a circuit that amplifies the electric signals produced from the light-receiving portion 303. An A/D converter 306 is a circuit by which the output signals from the amplifier 304 are converted to digital signals. A two-wavelength measurement control circuit 307 outputs signals that allow the two LEDs in the light source assembly 301 to be actuated in succession to emit light at predetermined timings. The signals from the control circuit 307 are also supplied to the amplifier 304, A/D converter 306, illumination intensity computing and storing circuit 309 and hemoglobin computing circuit 310.

The illumination intensity computing and storing circuit 309 determines the ratio, $R_{12}$, between the intensities of emitted light component of wavelengths $\lambda_1$ and $\lambda_2$. The hemoglobin computing circuit 310 computes the level of hemoglobin in the tissue HbDb on the basis of both $It_1$ and $It_2$ (the intensities of light components at $\lambda_1$ and $\lambda_2$ which have been transmitted through the living tissue of interest) supplied from the A/D converter 306 and $R_{12}$ that has been determined by the circuit 309. A hemoglobin concentration memory circuit 320 stores the supplied hemoglobin concentration Hb. A blood computing circuit 319 computes the quantity of blood in the tissue Db on the basis of both HbDb as calculated by the hemoglobin computing circuit 310 and Hb as stored in the hemoglobin concentration memory circuit 320.

A selection switch 308 is operated in such a way that the output from the A/D converter 306 is selectively supplied to either the illumination intensity computing and storing circuit 309 or the hemoglobin computing circuit 310. The selecting operation of the switch 308 is controlled by a calibration/measurement mode selection control circuit 311.

A display unit 312 and a recorder 313 will respectively display and record the results of calculation by the hemoglobin computing circuit 310 and the blood computing circuit 320.

The procedure of operating the system shown in FIG. 5 is next described below. First, the operator activates the hemoglobin concentration memory circuit 320 to store the hemoglobin concentration of the subject under assay. He then provides a light attenuating plate 315 between the two-wavelength light source assembly 301 and the light-receiving portion 330. Then, he activates the calibration/measurement mode selection control circuit 311 and places the switch 308 in such a position that the A/D converter 306 is connected to the illumination intensity computing and storing circuit 309. Subsequently, the operator causes the two-wavelength measurement control circuit 307 to start the control mode, whereupon the two-wavelength light source assembly 301, amplifier 304, A/D converter 306, illumination intensity computing and storing circuit 309 and hemoglobin computing circuit 310 are controlled by control signals being supplied from the two-wavelength measurement control circuit 307. Stated more specifically, the light source assembly 301 emits light at the wavelengths $\lambda_1$ (805 nm) and $\lambda_2$ (890 nm) at predetermined intervals. The individual components of the emitted light pass through the attenuating plate 315 and are incident on the light-receiving portion 303, where they are converted to electric signals. The amplifier 304, A/D converter 306 and illumination intensity computing and storing circuit 309 will operate in synchronism with the timing at which the two-wavelength light source assembly 301 is lit. The signals thus supplied to the illumination intensity computing and storing circuit 309 correspond to $Ie_1$ and $Ie_z$ in eq. (309), from which the circuit 309 calcualates $Ie_1/Ie_2 = R_{12}$ for storage.

In the next step, the operator removes the plate 315 and in its stead provides a living tissue of interest 317 (e.g. a finger or earlobe) between the two-wavelength light source assembly 301 and the light-emitting portion 303. He then activates the calibration/measurement mode selection control circuit 311 and places the switch 308 in such a position that the A/D converter 306 is connected to the hemoglobin computing circuit 310. Subsequently, the operator causes the two-wavelength measurement control circuit 307 to start the control mode. As in the case of measuring the intensity of illuminating light using the attenuation plate 315, the A/D converter 306 supplies the hemoglobin computing circuit 310 with output signals that correspond to $It_1$ and $It_2$.

On the basis of the values of $It_1$ and $It_2$, as well as $R_{12}$ which is stored in the illumination intensity computing and storing circuit 309, the hemoglobin computing circuit 310 performs calculation by eq. (324) ($R_{12}$ is included in $Io_1$ in eq. (324)), thereby determing the level of hemoglobin in the tissue HbDb. The blood computing circuit 319 determines the quantity of blood in the tissue Db by eq. (325) both from HbDb as calculated by the circuit 310 and from Hb or the hemoglobin concentration stored in the circuit 320. The thus determined quantities of hemoglobin and blood are displayed on the display unit 312 and recorded by the recorder 313.

In the embodiment under consideration, the light attenuating plate 315 is used to measure the intensity of emitted illuminating light and, therefore, the measuring instrument may be the same as what is used to measure the intensity of light that has been transmitted through the living tissue 317. The plate 315 desirably causes light to be attenuated by the same degree at each of the operating wavelengths of the light source assembly; however, even if the plate causes different degrees of attenu-ating, there is no problem at all if the differences are known and can be corrected by the means of computing the intensity ratio of emitted light.

In the described case, the light components of two wavelengths are successively generated but, if desired, they may be generated alternately at very short intervals and received by a means that reproduces the signals representing the respective wavelengths as separate entities. The result of this modification is the same as what is achieved by processing the light components of two wavelengths that have been generated almost simultaneously.

In the embodiment under consideration, the light emitted from the three-wavelength light source assembly 301 has already passed through the scattering plate and, hence, there is no possibility that the absorbance rate of light varies in a shallow and a deep area of the living tissue under examination.

The embodiment has another advantage in that using the intensity ratio of emitted light, it is less subjected to the effect of measuring conditions. A further advantage of the embodiment is that being capable of measuring and storing the intensity of illumination at a suitable time, it is by no means susceptible to the adverse effects of aging or fouling of the light-emitting portion.

It should also be noted that $Eh_2$ is defined by approximation in the embodiment at issue but this causes no error if the oxygen saturation S is 1 (100%). As the oxygen saturation decreases, the error will increase but this does not cause any serious effect since the permissible error is great at lower levels of oxygen saturation.

If the oxygen saturation S cannot be regarded as substantially 100%, the approximation $Eh_2 = Eo_2$ cannot be adopted as in the embodiment described above since $Eb_2$ in eq. (320) varies with S. In this case, the oxygen saturation S must be determined using light components of three wavelengths and, on the basis of the determined S, $Eh_2$ is determined as follows:

$$Eh_2 = SEo_2 + (1-S)Er_2 \quad (326)$$

On the basis of this $Eh_2$, we obtain:

$$Eb_2 = \{Eh_2(Eh_2+f)\}^{\frac{1}{2}} \quad (327)$$

Using this equation, one can determine $\log Io_1$ in eq. (320). Substituting the thus determined $\log Io_1$ into eqs. (324) and (325), one can determine the quantities of both hemoglobin and blood in the tissue under examination.

We now describe the principle of determining S using light components of three wavelengths. According to Schuster's theory, the degrees of light attenuation, $A_1$, $A_2$ and $A_3$, for the respective wavelengths are as follows:

$$A_1 = \log(Ie_1/It_1) \quad (328)$$
$$= \{Eh_1Hb(Eh_1Hb + G)\}^{\frac{1}{2}}Db + ZtDt$$

$$A_2 = \log(Ie_2/It_2) \quad (329)$$
$$= \{Eh_2Hb(Eh_2Hb + G)\}^{\frac{1}{2}}Db + ZtDt$$

$$A_3 = \log(Ie_3/It_3) \quad (330)$$
$$= \{Eh_3Hb(Eh_3Hb + G)\}^{\frac{1}{2}}Db + ZtDt$$

where $$\psi = (A_3 - A_2)/(A_1 - A_2) \tag{331}$$

Eq. (331) is expanded as follows by eqs. (328), (329) and (330):

$$\psi = \{\log(Ie_3/Ie_2) - \log(It_3/It_2)\}/\{\log(Ie_1/Ie_2) - \log(It_1/It_2)\} \tag{332}$$

Looking at eqs. (328), (329) and (330), eq. (331) can also be rewritten as follows:

$$\psi = [\{Eh_3Hb(Eh_3Hb + G)\}^{\frac{1}{2}} - \{Eh_2Hb(Eh_2Hb + G)\}^{\frac{1}{2}}]/[\{Eh_1Hb(Eh_1Hb + G)\}^{\frac{1}{2}} - \{Eh_2Hb(Eh_2Hb + G)\}^{\frac{1}{2}}] \tag{333}$$

If the concentration of hemoglobin is not abnormally high, namely in the case where Hb < 20 (g/dL), G may as well be considered to be equal to FHb. Using this relationship, eq. (333) can be rewritten as:

$$\psi = [\{Eh_3(Eh_3 + F)\}^{\frac{1}{2}} - \{Eh_2(Eh_2 + F)\}^{\frac{1}{2}}]/[\{Eh_1(Eh_1 + F)\}^{\frac{1}{2}} - \{Eh_2(Eh_2 + F)\}^{\frac{1}{2}}] \tag{334}$$

If the three wavelengths $\lambda_1$, $\lambda_2$ and $\lambda_3$ are set at 805 nm, 890 nm and 650 nm, respectively, the following relationships are valid:

$$Eh_1 = Eo_1 \tag{335}$$

$$\begin{aligned} Eh_2 &= SEo_2 + (1 - S)Er_2 \\ &= S(Eo_2 - Er_2) + Er_2 \\ &= Er_2 - S\Delta E_2 \end{aligned} \tag{336}$$

$$Eh_3 = Er_3 - S\Delta E_3 \tag{337}$$

where $\Delta E = Eo - Er$.

Using eqs. (335), (336) and (337), eq. (334) can be rewritten as:

$$\psi = [\{(Er_3 - S\Delta E_3)(Er_3 - S\Delta E_3 + F)\}^{\frac{1}{2}} - \{(Er_2 - S\Delta E_2)(Er_2 - S\Delta E_2 + F)\}^{\frac{1}{2}}]/[\{Eo_1(Eo_1 + F)\}^{\frac{1}{2}} - \{(Er_2 - S\Delta E_2)(Er_2 - S\Delta E_2 + F)\}^{\frac{1}{2}}] \tag{338}$$

Starting with unity, numerals that decrease by increments of a certain value, say, 0.01 are substituted into S on the right side of eq. (338); each of the computed values of the right side is compared with $\psi$ on the left side; when $\psi$ is exceeded, the pertinent value of S is defined as the oxygen saturation S of the living tissue of interest.

Figure 6:
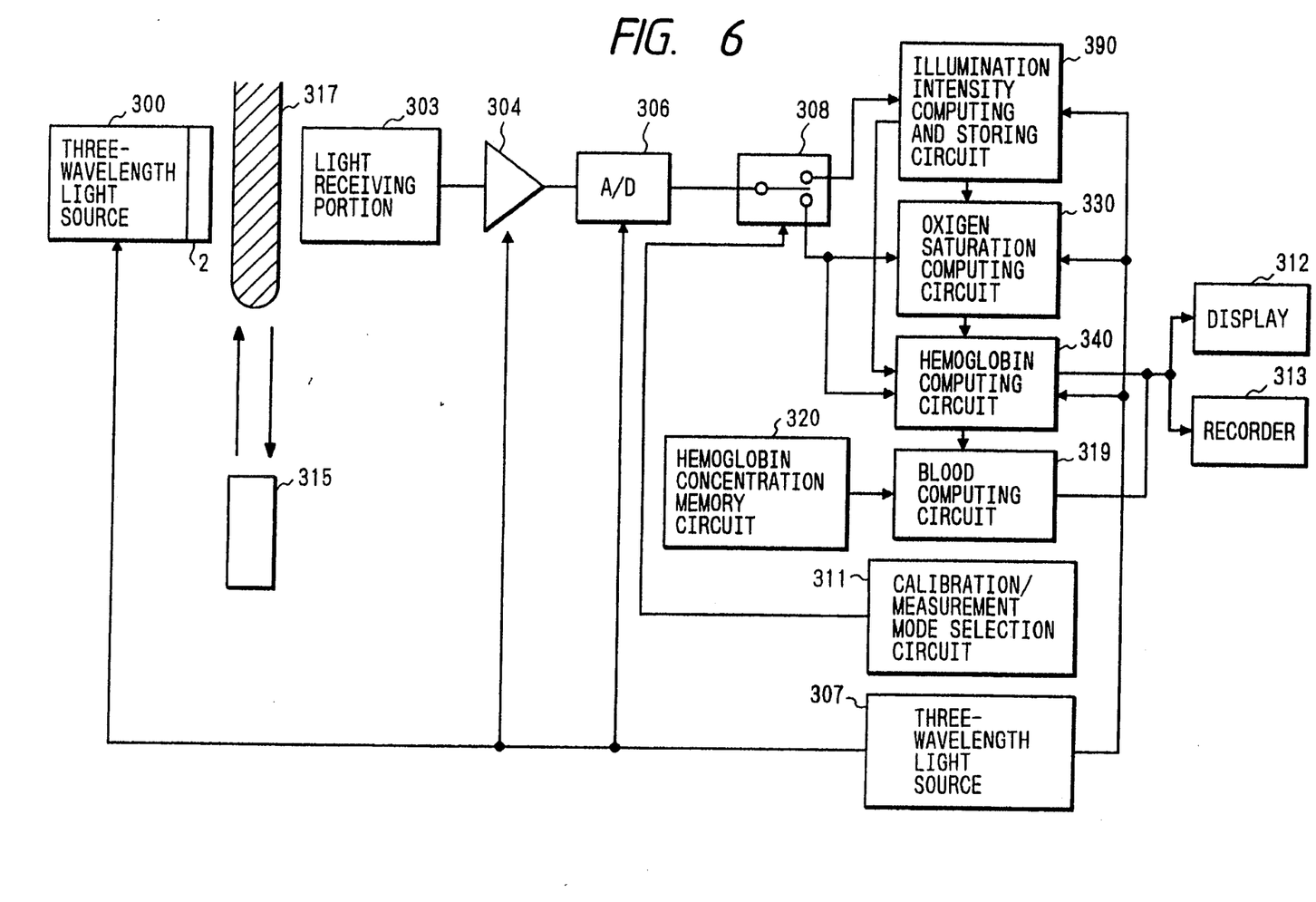
FIG. 6 is a block diagram showing the overall composition of another system in which the concept of the present invention is applied to an apparatus for measuring the level of hemoglobin in tissue.

An apparatus that may advantageously be used for measuring the level of hemoglobin in tissue when its oxygen saturation S is not substantially 100% is shown schematically in FIG. 6.

The apparatus shown in FIG. 6 is identical to what is shown in FIG. 5 except on the following points: (1) the living organism 317 is illuminated with light that is emitted from a three-wavelength light source assembly 300; (2) the on-off control of the assembly 300 is performed with a three-wavelength measurement control circuit 307; (3) the ratios between the intensities of emitted light components at different wavelengths are calculated and stored by an illumination intensity computing and storing circuit 390 that performs its function for three wavelengths; (4) the apparatus is furnished with an oxygen saturation computing circuit 330 that calculates the oxygen saturation S on the basis of both the ratios between the intensities of emitted light components at the three wavelengths and the intensities of the components of light transmitted through the living organism at the respective wavelengths; and (5) the hemoglobin level is calculated by a hemoglobin computing circuit 340 on the basis of the intensity ratios of emitted light stored in the illumination intensity computing and storing circuit 390, the value of S calculated by the oxygen saturation computing circuit 330 and the intensities of the components of light transmitted through the living tissue at the three wavelengths. The three-wavelength light source assembly 300 may typically emit light components at $\lambda_1 = 805$ nm, $\lambda_2 890$ nm and $\lambda_3 = 650$ nm.

The procedure of operating the system shown in FIG. 6 is next described below. First, the operator provides the light attenuating plate 315 between the three-wavelength light source assembly 300 and the light-receiving portion 330. He then activates the calibration/measurement mode selection control circuit 311 and places the switch 308 in such a position that the A/D converter 306 is connected to the illumination intensity computing and storing circuit 309. Subsequently, the operator causes the three-wavelength measurement control circuit 307 to start the control mode, whereupon the three-wavelength light source assembly 300, illumination intensity computing and storing circuit 390, oxygen saturation computing circuit 330 and A/D converter 306 are controlled by control signals being supplied from the three-wavelength measurement control circuit 307. Stated more specifically, the light source assembly 300 will emit light as the wavelength $\lambda_1$, (805 nm), $\lambda_2$ (890 nm) and $\lambda_3$ (650 nm) at predetermined intervals. The individual components of the emitted light pass through the attenuating plate 315 and are incident on the light-receiving portion 303, where they are converted to electric signals. The amplifier 304, A/D converter 306 and the illumination intensity computing and storing circuit 390 will operate in synchronism with the timing at which the three-wavelength light source assembly is lit. The signals thus supplied to the illumination intensity computing and storing circuit 390 correspond to $Ie_1$, $Ie_2$ and $Ie_3$, from which the illumination intensity computing and storing circuit 390 calculates $Ie_3/Ie_2$ and $Ie_1/Ie_2$ for storage.

In the next step, the operator removes the plate 315 and in its stead provides the living tissue 317 (e.g., a finger or earlobe) between the three-wavelength light source assembly 300 and the light-receiving portion 330. He then activates the calibration/measurement mode selection control circuit 311 and places the switch 308 in such a position that the A/D converter 306 is connected to the oxygen saturation computing circuit 330. Subsequently, the operator causes the three-wavelength measurement control circuit 307 to start the control mode. As in the case of measuring the intensity of illuminating light using the attenuation plate 315, the A/D converter 306 supplies the oxygen saturation computing circuit 330 with output signals that correspond to $It_1$, $It_2$ and $It_3$. The oxygen saturation computing circuit 330 determines $\psi$ by substituting the following five parameters into eq. (329): $Ie_3/Ie_2$ and $Ie_1/Ie_2$ stored in the illumination intensity computing and storing circuit 390, as well as $It_1$, $It_2$ and $It_3$ supplied from the A/D converter 306. The oxygen saturation computing circuit 330 then performs the following operation: starting with unity, numerals that decrease by increments of a certain value, say, 0.01 are substituted into S on the right side of eq. (332); each of the computed values of the right side is compared with $\psi$ on the left side; when $\psi$ is exceeded, the pertinent value of S is supplied as output to the hemoglobin computing circuit 340. The hemoglobin computing circuit 340 substitutes the supplied S into eq. (326) to determine $Eh_2$, which is substituted into eq. (327) to determine $Eb_2$. In the next step, the hemoglobin computing circuit 340 determines log $Io_1$ by performing calculation on eq. (320) using $It_1$ and $It_2$ supplied from the A/D converter 306, $Ie_1/Ie_2$ ($=R_{12}$) stored in the illumination intensity computing and storing circuit 309 and the determined $Eb_2$. The hemoglobin level HbDb is calculated by eq. (324) from the thus determined log $Io_1$ and the given $It_1$. On the basis of the calculated hemoglobin level, the blood computing circuit 319 calculates the blood level Db and, further, HbDb is displayed on the display unit 312 and recorded by the recorder 313 as in the embodiment already described with reference to FIG. 5.

In the embodiments described on the foregoing pages, various calculations and controls are performed by independent circuits but they may be implemented by a computer.

According to the third embodiment of the present invention, the quantity of hemoglobin or blood in a tissue under assay can be determined in a quantitative manner.

What is claimed is:

1. An apparatus for measuring a predetermined data of living tissue comprising:
   a means for illuminating said living tissue with light emitting at at least three wavelengths;
   a photoelectric transducing means for receiving light transmitted through said tissue and for converting said light transmitted through said tissue to electric signals;
   a memory means for storing data of said illuminating light emitting at the three wavelengths, said illuminating light not transmitted through said living tissue; and
   a computing means for calculating said predetermined data of living tissue on the basis of the output from said photoelectric transducing device, representing light transmitted through said living tissue, and said data of illuminating light stored in said memory device, representing light not transmitted through said living tissue;
   wherein said computing means calculates ratios between intensities of illuminating light emitting at the three wavelengths on the basis of the data stored in said memory means.

2. An apparatus for measuring a predetermined data of living tissue as claimed in claim 1, wherein said data includes ratios between intensities of said illuminating light emitting at the three wavelengths that are stored in said memory means.

3. An apparatus for measuring a predetermined data of living tissue as claimed in claim 1, wherein said data includes intensities of said illuminating light emitting at the three wavelengths that are stored in said memory means.

4. An apparatus for measuring a predetermined data of a living tissue as claimed in claim 1, wherein said illuminating means has a scattering plate, through which said light emitting at the three wavelengths is caused to pass before illuminating said living tissue.

5. An apparatus for measuring a predetermined data of a living tissue as claimed in claim 1, wherein the light from said illumination means is passed through a light attenuating plate having known attenuation characteristics.

6. An apparatus for measuring a predetermined data as claimed in claim 1, wherein said predetermined data includes at least one of an oxygen saturation of blood, the level of hemoglobin of blood in tissue and a pigment concentration.

7. An apparatus for measuring a predetermined data of a living tissue comprising:
   a light generating means for generating light having at least two wavelengths;
   a photoelectric transducing means for converting said light emitted from said light generating means to electric signals, said photoelectric transducing means being spaced from said light generating means;
   an intensity ratio computing means for calculating the intensity ratio of the light components at respective wavelengths that are emitted from said light generating means on the basis of the signals output from said photoelectric transducing means and are not transmitted through living tissue;
   a memory means for storing the intensity ratio calculated by said intensity ratio computing means; and
   a computing means for performing predetermined calculations on the basis of both the output from said photoelectric transducing means, representing light components which are transmitted through living tissue, and the intensity ratio stored in said memory means, representing light components which are not transmitted through living tissue, when a living tissue is inserted in the space between said light generating means and said photoelectric transducing means, thereby determining a level of said predetermined data.

8. An apparatus for measuring a predetermined data as claimed in claim 7 further comprising:
   a light attenuating plate having predetermined attenuation characteristics, wherein
   said intensity ratio computing means calculates the predetermined data on the basis of the signals output from said photoelectric transducing means when the said light attenuating plate is inserted between said light generating means and said photoelectric transducing means.

9. An apparatus for measuring a predetermined data of living tissue as claimed in claim 8 wherein said light generating means has a scattering plate, through which light components of the respective wavelengths are caused to pass before they are received by the photoelectric transducing means.

10. An apparatus for measuring a predetermined data of living tissue as claimed in claim 8, wherein said predetermined data include the level of hemoglobin or blood.

* * * * *